United States Patent
Singh et al.

(10) Patent No.: US 9,399,661 B2
(45) Date of Patent: Jul. 26, 2016

(54) TETRAPEPTIDE COPPER CATALYSTS CAPABLE OF OXIDIZING HYDROCARBONS AT ROOM TEMPERATURE

(71) Applicant: University of the West Indies, St. Augustine (TT)

(72) Inventors: Gurdial Singh, St. Augustine (TT); Latisha Candice Nicholas-Lewis, Sangre Grande (TT)

(73) Assignee: University of The West Indies, St. Augustine (TT)

( * ) Notice: Subject to any disclaimer, the term of this patent is extended or adjusted under 35 U.S.C. 154(b) by 0 days.

(21) Appl. No.: 14/815,303

(22) Filed: Jul. 31, 2015

(65) Prior Publication Data

US 2016/0060292 A1    Mar. 3, 2016

Related U.S. Application Data

(60) Provisional application No. 62/034,566, filed on Aug. 7, 2014.

(51) Int. Cl.
*C07C 29/50* (2006.01)
*C07K 5/103* (2006.01)
*B01J 31/18* (2006.01)
*C07C 29/48* (2006.01)
*C07C 45/33* (2006.01)

(52) U.S. Cl.
CPC ............. *C07K 5/1008* (2013.01); *B01J 31/181* (2013.01); *B01J 31/1825* (2013.01); *C07C 29/48* (2013.01); *B01J 2231/70* (2013.01); *B01J 2531/16* (2013.01); *C07C 29/50* (2013.01); *C07C 45/33* (2013.01)

(58) Field of Classification Search
CPC ................................. C07C 29/50; C07C 45/33
USPC .................................................. 568/910, 910.5
See application file for complete search history.

(56) References Cited

U.S. PATENT DOCUMENTS

| 4,539,155 | A | * | 9/1985 | Kitaura | ................. | C07C 243/00 530/332 |
| 4,801,580 | A | * | 1/1989 | Kitaura | ................. | C07C 243/00 530/330 |

* cited by examiner

*Primary Examiner* — Elvis O Price
(74) *Attorney, Agent, or Firm* — Wilmer Cutler Pickering Hale and Dorr LLP

(57) ABSTRACT

The present invention relates to peptide copper catalysts capable of oxidizing hydrocarbons at room temperature.

28 Claims, 7 Drawing Sheets

TETRAPEPTIDE COPPER CATALYSTS CAPABLE OF OXIDIZING HYDROCARBONS AT ROOM TEMPERATURE

CROSS-REFERENCE TO RELATED APPLICATION

This application claims benefit under 35 U.S.C. §119(e) of U.S. Provisional Patent Application No. 62/034,566, filed on Aug. 7, 2014 which is hereby incorporated by reference in its entirety.

FIELD OF THE INVENTION

This application relates generally to peptide copper catalysts. More specifically, the application relates to the use of peptide copper catalysts capable of the oxidation of hydrocarbons at room temperature.

BACKGROUND OF THE INVENTION

Due to the rapid depletion of natural resources, the need to access alternative fuels remains a great priority. Methanol is an example of an alternative fuel. The methanol industry is driven in part by the rising demand for alternative fuel and cleaner energy. Methanol is also used in a number of chemical intermediates that are utilized to make numerous products throughout the global economy.

The chemical oxidation of petroleum and natural gas hydrocarbons to alternative fuels and useful chemical intermediates would be a process of great industrial value affecting global energy use and the worldwide economy. However, current oxidative transformations of hydrocarbons are inefficient or costly synthetic protocols. The oxidation of petroleum and natural gas hydrocarbons are problematic largely due to the high bond energy of the C—H bond which renders hydrocarbons unreactive to chemical transformations. For example, methane has a bond energy of 104 kcal/mol and ethane has a bond energy of 101 kcal/mol. The development of efficient and low cost methods using catalysts that easily oxidize unreactive hydrocarbons, such as methane and ethane, would provide a useful approach to overcome the current challenges for the production of alternative fuels and useful chemical intermediates.

Recent developments in methane oxidation have recognized the value of using catalysts that oxidize unreactive hydrocarbons. However, these transformations require heating to elevated temperatures at high pressure. Moreover, these transformations require the use of highly dangerous concentrated sulfuric acid. Some methods have demonstrated catalytic production of methanol from methane; however, poor catalytic turnover numbers render these transformations inefficient and hinder its industrial application.

A more desirable approach to the catalytic oxidation of unreactive hydrocarbons is to provide a method that is conducted at ambient temperature and pressure using accessible reagents such as water and oxygen. It is necessary for the catalyst to be readily accessible from low-cost precursors and demonstrate high turnover numbers for efficiency which would provide a viable method to mitigate the current challenges for the process of alternative fuels and useful chemical intermediates.

The present invention overcomes the problems of the past and provides a novel method for the catalytic oxidation of hydrocarbons using peptide copper catalysts.

SUMMARY OF THE INVENTION

It is understood that any of the embodiments described below can be combined in any desired way, and that any embodiment or combination of embodiments can be applied to each of the aspects described below, unless the context indicates otherwise.

In at least one embodiment, the invention provides a catalyst containing a copper metal and peptide, the peptide is a tetrapeptide or pentapeptide capable of catalytic oxidation of a hydrocarbon.

In some embodiments, the catalyst containing a copper metal and peptide, the peptide is a tetrapeptide.

In some embodiments, the catalyst containing a copper metal and peptide, the peptide is a straight chain tetrapeptide comprising four amino acids.

In some embodiments, the straight chain tetrapeptide comprises four amino acids selected from the group consisting of Alanine, Aspartate, Glutamate, Glycine, Histidine, Methionine and Tryptophan.

In some embodiments, the straight chain tetrapeptide comprises four amino acids selected from the group consisting of Alanine, Aspartate, Glutamate, Histidine, Methionine and Tryptophan.

In some embodiments, the straight chain tetrapeptide comprises four amino acids selected from the group consisting of Alanine, Glutamate and Histidine.

In some embodiments, the straight chain tetrapeptide comprises four amino acids selected from the group consisting of Alanine, Aspartate, Methionine and Tryptophan.

In some embodiments, the straight chain tetrapeptide comprises four amino acids having at least Glutamate and Histidine.

In some embodiments, the peptide is selected from any one of the following straight chain tetrapeptides having a peptide sequence comprising: AlaHisAlaGlu; AlaMetAspTrp; AlaHisGlyGlu; AlaHisHisHis; GlyHisHisHis; GluHisAspHis; HisMetAspTrp; and AspHisAspHis.

In some embodiments, the peptide is selected from any one of the following straight chain tetrapeptides having a peptide sequence comprising: AlaHisAlaGlu; and AlaMetAspTrp.

In at least one embodiment, the invention provides a method for catalytic oxidation of a hydrocarbon using a catalyst containing a copper metal and peptide, the peptide is a tetrapeptide or pentapeptide is capable of catalytic oxidation of a hydrocarbon.

In some embodiments, the method for catalytic oxidation of a hydrocarbon using a catalyst containing a copper metal and peptide, the peptide is a tetrapeptide.

In some embodiments, the method for catalytic oxidation of a hydrocarbon using a catalyst containing a copper metal and tetrapeptide, the tetrapeptide is a straight chain tetrapeptide comprising four amino acids.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Aspartate, Glutamate, Glycine, Histidine, Methionine and Tryptophan.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Aspartate, Glutamate, Histidine, Methionine and Tryptophan.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Glutamate and Histidine.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Aspartate, Methionine and Tryptophan.

In some embodiments, the method for catalytic oxidation of a hydrocarbon using a catalyst containing a copper metal and a straight chain tetrapeptide, the straight chain tetrapeptide comprises four amino acids having at least Glutamate and Histidine.

In some embodiments, the method for catalytic oxidation of a hydrocarbon using a catalyst containing a copper metal and a peptide, the peptide is selected from any one of the following tetrapeptides having a peptide sequence comprising: AlaHisAlaGlu; AlaMetAspTrp; AlaHisGlyGlu; AlaHisHisHis; GlyHisHisHis; GluHisAspHis; HisMetAspTrp; and AspHisAspHis.

In some embodiments, the method for catalytic oxidation of a hydrocarbon using a catalyst containing a copper metal and a peptide, the peptide is selected from any one of the following tetrapeptides having a peptide sequence comprising: AlaHisAlaGlu; and AlaMetAspTrp.

In some embodiments, the hydrocarbon is methane or ethane.

In some embodiments, the hydrocarbon is methane.

In some embodiments, the catalytic oxidation is performed with water and oxygen gas at ambient temperature and pressure.

In some embodiments, the catalytic oxidation is performed with water and oxygen gas.

In some embodiments, the catalytic oxidation is performed at ambient temperature and pressure.

In some embodiments, the catalytic oxidation is performed at a temperature of 20-43° C.

In some embodiments, the catalytic oxidation is performed at a pressure of 1-10 Atm.

In some embodiments, the catalytic oxidation is performed at a temperature of 20-43° C. and at a pressure of 1-10 Atm.

In some embodiments, the water is distilled or heavy water ($D_2O$).

In some embodiments, the methane is catalytically oxidized to methanol.

In some embodiments, the ethane is catalytically oxidized to ethanol.

The details of the invention are set forth in the accompanying description below.

DETAILED DESCRIPTION OF THE INVENTION

Definitions and Abbreviations

Figure 1:
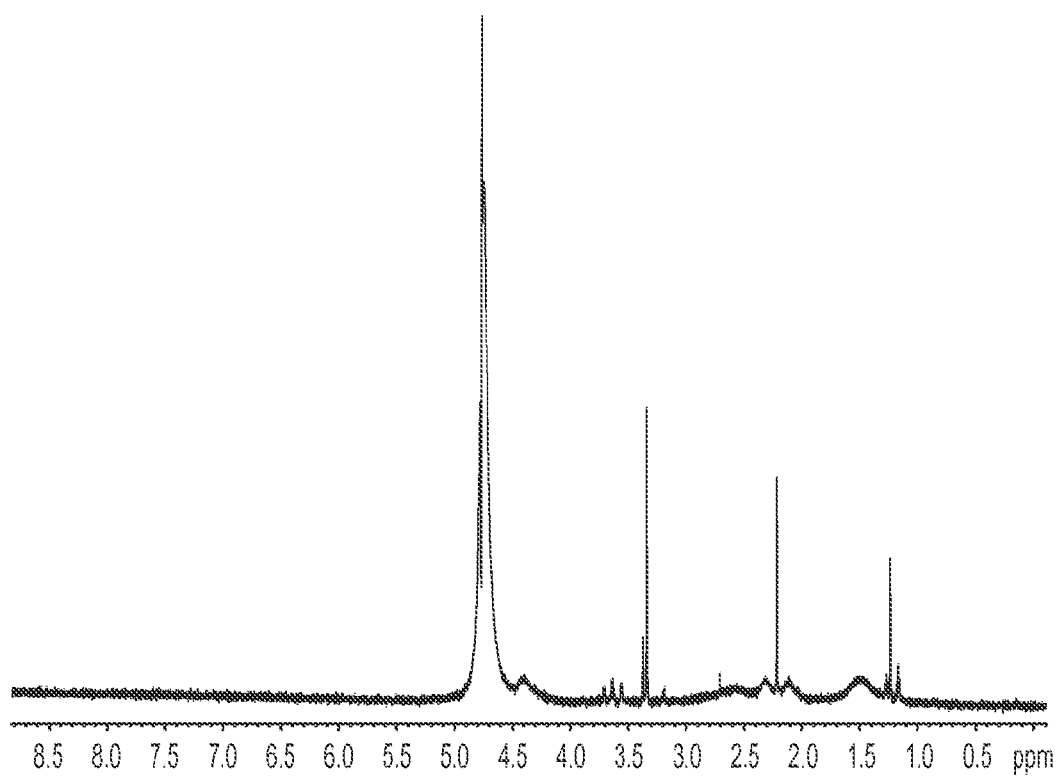
FIG. 1 shows a representative $^1$HNMR spectra of a Cu(II)(AlaHisAlaGlu) catalyst with oxygen.

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The term "hydrocarbon" as used herein, refers to a straight chain or branched non-cyclic compound that contains only carbon and hydrogen. Representative straight chain hydrocarbon includes methane, ethane, n-propane, n-butane, n-pentane and n-hexane. Representative branched hydrocarbon include isopropane, sec-butane, isobutene, tert-butane, isopentane, neopentane, 1-methylbutane, isohexane, neohexane, 2-methylbutane, 3-methylbutane, 1,1-dimethylpropane and 1,2-dimethylpropane. In one embodiment, the hydrocarbon is substituted.

All configurational isomers of the compounds described herein are contemplated, either in admixture or in pure or substantially pure form. Certain compounds described herein may exist in particular geometric or stereoisomeric forms. The present invention contemplates all such compounds, including cis- and trans-isomers, cis (Z) and trans (E) alkene isomers R- and S-enantiomers, diastereomers, (D)-isomers, (L)-isomers, the racemic mixtures thereof, and other mixtures thereof, as falling within the scope of the invention. Additional asymmetric carbon atoms may be present in a substituent. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

Definitions of specific functional groups and chemical terms are described in more detail above. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999, the entire contents of which are incorporated herein by reference.

In some embodiments, the present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon and oxygen, such as $^2$H, $^3$H, $^{13}$C, $^{11}$C, $^{14}$C, $^{18}$O and $^{17}$O, respectively. Compounds described herein, or an enantiomer, diastereomer, which contain the aforementioned isotopes and/or other isotopes of other atoms, are within the scope of this invention. Isotopically labeled compounds can generally be prepared by carrying out the procedures disclosed in the Schemes and/or in the Examples below, by substituting a readily available isotopically labeled reagent for a non-isotopically labeled reagent.

When more than one position in any given structure may be substituted with more than one substituent selected from a specified group, the substituent may be either the same or different at every position.

The term "peptide" as used herein, refers to a straight chain, cyclic or non-cyclic compound that contains natural and unnatural amino acids. Representative straight chain peptides include tetrapeptide and pentapeptide. In one embodiment, the straight chain tetrapeptide comprises four amino acids. In another embodiment, the straight chain pentapeptide comprises five amino acids.

Abbreviations

Abbreviations used in the following examples and preparations include:
A Alanine
Ala Alanine
aq Aqueous
arom Aromatic
Asp Aspartate
Atm Atmosphere
Bn Benzyl
Boc Tert-Butoxycarbonyl
C-terminal Carboxyl-Terminal
D Aspartate
d Doublet
DCM Dichloromethane
dd Doublet of Doublets
DMAP 4-(Dimethylamino)pyridine
dt Doublet of Triplets
E Glutamate
EDC 1-Ethyl-3-(3-dimethylaminopropyl)carbodiimide
Et Ethyl
Et$_3$N Triethylamine
equiv Equivalent
ESI Electrospray Ionization
G Glycine
g Grams(s)
GC Gas chromatography
Glu Glutamate
Gly Glycine
H Histidine
hr Hour
hrs Hour(s)
His Histidine
HOsucc N-hydroxysuccinimide
HPLC High Pressure Liquid Chromatography
HSQC heteronuclear Single Quantum Coherence
Im Imidazole
LC-MS Liquid Chromatography-Mass Spectrometry
LG Leaving Group
M Methionine
m Multiplet
Me Methyl
Met Methionine
mins Minute(s)
ml Milliliter
mM Millimolar
mmol Millimoles
MS Mass Spectrometry
MW Molecular Weight (all values are ±0.05)
NMR Nuclear Magnetic Resonance
N-terminal Amine-Terminal
OTf Triflate
psi Pounds Per Square Inch
q Quartet
RB Round Bottom
RT Room Temperature (about 20-25° C.)
s Singlet
t Triplet
TEA Triethylamine
TFA Trifluoroacetic Acid
Trp Tryptophan
ul Microliter
UV-VIS Ultraviolet-Visible Spectroscopy
W Tryptophan Peptide Copper Catalysts Described below are peptide copper catalysts, as well as methods that may be useful for preparing the catalysts and using the catalysts to oxidize hydrocarbons, such as methane and ethane. The peptide copper catalysts of the disclosure are believed to oxidize hydrocarbons, i.e., peptide copper catalysts that oxidize methane to methanol.

In at least one embodiment, the invention provides a peptide copper catalyst that catalytically oxidize methane to methanol.

In at least one embodiment, the invention provides a method for catalytic oxidation performed with water and oxygen gas at ambient temperature and pressure.

In at least one embodiment, the invention provides a catalyst containing a copper metal and peptide, the peptide is a tetrapeptide or pentapeptide capable of catalytic oxidation of a hydrocarbon.

In some embodiments, the catalyst containing a copper metal and peptide, the peptide is a tetrapeptide.

In some embodiments, the catalyst containing a copper metal and peptide, the peptide is a straight chain tetrapeptide comprising four amino acids.

In some embodiments, the straight chain tetrapeptide comprises four amino acids selected from the group consisting of Alanine, Aspartate, Glutamate, Glycine, Histidine, Methionine and Tryptophan.

In some embodiments, the straight chain tetrapeptide comprises four amino acids selected from the group consisting of Alanine, Aspartate, Glutamate, Histidine, Methionine and Tryptophan.

In some embodiments, the straight chain tetrapeptide comprises four amino acids selected from the group consisting of Alanine, Glutamate and Histidine.

In some embodiments, the straight chain tetrapeptide comprises four amino acids selected from the group consisting of Alanine, Aspartate, Methionine and Tryptophan.

In some embodiments, the straight chain tetrapeptide comprises four amino acids having at least Glutamate and Histidine.

In some embodiments, the peptide is selected from any one of the following straight chain tetrapeptides having a peptide sequence comprising: AlaHisAlaGlu; AlaMetAspTrp; AlaHisGlyGlu; AlaHisHisHis; GlyHisHisHis; GluHisAspHis; HisMetAspTrp; and AspHisAspHis.

In some embodiments, the peptide is selected from any one of the following straight chain tetrapeptides having a peptide sequence comprising: AlaHisAlaGlu; and AlaMetAspTrp.

Methods for Making Peptide Copper Catalysts

Methods useful for making the peptide copper catalysts are set forth in the Examples below and generalized in the procedures below. These procedures are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety. For example, the following procedures are illustrations but not limitations of the preparation of some of the starting materials and exemplary compounds described herein. Various modifications to these methods may be envisioned by those skilled in the art to achieve similar results to those provided below. For example, optional protecting groups can be used as described, for example, in Greene et al., *Protective Groups in Organic Synthesis* ($3^{rd}$ ed. 1999). Processes for the preparation of tetrapeptides using solution phase synthesis, solid phase synthesis or biological synthesis can be used as described.

General Procedure for the Synthesis of Peptides Using the Mixed Anhydride Method To a solution of pivoyl (1.4 equiv) or $Boc_2O$ dissolved in 4 ml of dry dichloromethane (20 ml) were added consecutively N-terminal-protected amino acid (0.5 mmol, 1 equiv), N-hydroxysuccinimide (1 equiv), triethylamine (2 equiv) and DMAP (0.5 equiv). After 3.5 hrs the C-terminal-protected amino acid (1.2 equiv) was added and the mixture stirred at room temperature for 18 hrs. Chloroform (100 ml) or dichloromethane was added and the resultant solution was washed with water, 2% HCl (20 ml), a saturated $NaHCO_3$ solution and water dried over $MgSO_4$ filtered and evaporated to afford the peptide.

General Procedure for the Synthesis of Peptides Using EDC Method

Amino acid methyl ester and HCl (10 mmol) was dissolved in $CHCl_3$ (20 ml). To this triethylamine (TEA) (4 ml, 28.7 mmol) was added at 0° C. and the reaction mixture stirred for 15 mins. To the resultant mixture was added the Boc amino acid (10 mmol) in $CHCl_3$ (20 ml) followed by the carbodiimide EDC (10 mmol). The resultant mixture was allowed to warm to room temperature by removal of the ice bath and stirring continued for 12 hrs. Subsequently the reaction was filtered and the residue was washed with $CHCl_3$ (30 ml) and the washings were added to the filtrate. The resultant solution was washed with 5% $NaHCO_3$ (20 ml), 5% HCl (20 ml) and distilled $H_2O$ (20 ml). The organic layer was dried over anhydrous $Na_2SO_4$, filtered and evaporated in vacuo.

General Procedure for In Situ Complexation with Cu (II) Salts

Procedures for in situ complexation with Cu (II) salts, preferably, copper (II) chloride, or copper (II) triflate, or other copper (II) salts without the necessity to isolate the subsequently formed complex are described. A 0.15 mM solution of the peptide was prepared using the peptide and distilled or heavy water ($D_2O$). Similarly a solution of copper salts was prepared (0.12 mM). Salts utilized $Cu(OTf)_2$, $CuSO_4.5H_2O$ or $CuCl_2.H_2O$. An equal molar quantity of copper salt solution was then added to the flask containing the solubilized tetrapeptide. The reaction mixture was allowed to stir for 1 hour after which an aliquot was removed for analysis; NMR, GC, MS and UV-VIS.

TABLE I

Exemplary Peptides Used for Making Peptide Copper Catalysts

AlaMetAspTrp
AlaHisAlaGlu
AlaHisGlyGlu
AlaHisHisHis
GlyHisHisHis
GluHisAspHis

TABLE I-continued

Exemplary Peptides Used for Making Peptide Copper Catalysts

HisMetAspTrp
AspHisAspHis

Methods for Catalytic Oxidation of Methane to Methanol Using Peptide Copper Catalysts Described below are methods for using the peptide copper catalysts to catalytically oxidize hydrocarbons, such as methane and ethane. The peptide copper catalysts of the disclosure are believed to oxidize hydrocarbons, i.e., peptide copper catalysts that oxidize methane to methanol. These procedures are illustrative and are not meant to limit the possible techniques disclosed herein to one skilled in the art may use at the industrial level. Different methods will be evident to those skilled in the art. Various modifications to these methods may be envisioned by those skilled in the art to achieve similar results to those provided below.

In at least one embodiment, the invention provides a peptide copper catalysts to catalytically oxidize methane to methanol.

In at least one embodiment, the invention provides a method for catalytic oxidation performed with water and oxygen gas at ambient temperature and pressure.

In another aspect, at least one embodiment of the invention provides a method for catalytic oxidation of a hydrocarbon using a catalyst containing a copper metal and peptide, the peptide is a tetrapeptide or pentapeptide is capable of catalytic oxidation of a hydrocarbon thereof as described herein.

In some embodiments, the method for catalytic oxidation of a hydrocarbon using a catalyst containing a copper metal and peptide, the peptide is a tetrapeptide.

In some embodiments, the method for catalytic oxidation of a hydrocarbon using a catalyst containing a copper metal and tetrapeptide, the tetrapeptide is a straight chain tetrapeptide comprising four amino acids.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Aspartate, Glutamate, Glycine, Histidine, Methionine and Tryptophan.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Aspartate, Glutamate, Histidine, Methionine and Tryptophan.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Glutamate and Histidine.

In some embodiments, the method for catalytic oxidation of a hydrocarbon using a catalyst containing a copper metal and a straight chain tetrapeptide, the straight chain tetrapeptide comprises four amino acids selected from the group consisting of Alanine, Aspartate, Methionine and Tryptophan.

In some embodiments, the method for catalytic oxidation of a hydrocarbon using a catalyst containing a copper metal and a straight chain tetrapeptide, the straight chain tetrapeptide comprises four amino acids having at least Glutamate and Histidine.

In some embodiments, the method for catalytic oxidation of a hydrocarbon using a catalyst containing a copper metal and a peptide, the peptide is selected from any one of the following tetrapeptides having a peptide sequence comprising: AlaHisAlaGlu; AlaMetAspTrp; AlaHisGlyGlu; AlaHisHisHis; GlyHisHisHis; GluHisAspHis; HisMetAspTrp; and AspHisAspHis.

In some embodiments, the method for catalytic oxidation of a hydrocarbon using a catalyst containing a copper metal and a peptide, the peptide is selected from any one of the following tetrapeptides having a peptide sequence comprising: AlaHisAlaGlu; and AlaMetAspTrp.

In some embodiments, the hydrocarbon is methane or ethane.

In some embodiments, the hydrocarbon is methane.

In some embodiments, the catalytic oxidation is performed with water and oxygen gas at ambient temperature and pressure.

In some embodiments, the catalytic oxidation is performed with water and oxygen gas.

In some embodiments, the catalytic oxidation is performed at ambient temperature and pressure.

In some embodiments, the catalytic oxidation is performed at a temperature of 20-43° C.

In some embodiments, the catalytic oxidation is performed at a pressure of 1-10 Atm.

In some embodiments, the catalytic oxidation is performed at a temperature of 20-43° C. and at a pressure of 1-10 Atm.

In some embodiments, the water is distilled or heavy water ($D_2O$).

In some embodiments, the methane is catalytically oxidized to methanol.

In some embodiments, the ethane is catalytically oxidized to ethanol.

General Procedure for Catalytic Oxidation of Methane to Methanol Using Peptide Copper Catalysts Procedures for in situ complexation with Cu (II) salts, preferably, copper (II) chloride, or copper (II) triflate, or other copper (II) salts without the necessity to isolate the subsequently formed complex are described. A 0.15 mM solution of the peptide was prepared using the peptide and distilled or heavy water. Similarly, a solution of copper salts was prepared (0.12 mM). Salts utilized $Cu(OTf)_2$, $CuSO_4.5H_2O$, or $CuCl_2.H_2O$. An equal molar quantity of copper salt solution was then added to the flask containing the solubilized dipeptide. The reaction mixture was allowed to stir for 1 hour after which an aliquot was removed for analysis; NMR, GC, MS and UV-VIS. To the remainder reaction mixture oxygen was introduced by bubbling the oxygen gas (99.9% purity) through the system for one hour. A small aliquot was removed for analysis. To the resultant solution methane and oxygen gas were introduced simultaneously with the oxygen for 1-2 hours. The reaction mixture was monitored as above and the color changes noted. A pink or blue coloration was observed in the case of the $CuCl_2$ experiments. The production of methanol was confirmed via NMR and GC experiments.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain additional information, exemplification and guidance which can be adapted to the practice of this invention in its various embodiments and equivalents thereof. The examples do not limit the scope of the invention described in the claims.

EXAMPLES

Example 1

Synthesis of AlaHisAlaGlu

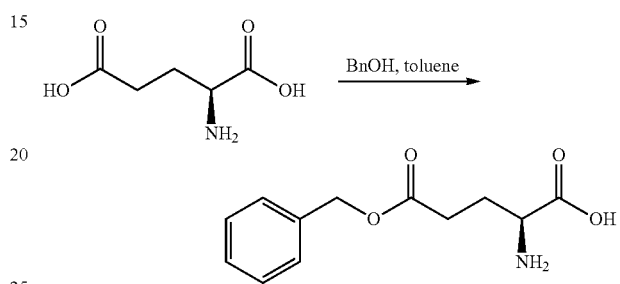

Synthesis of
(S)-2-amino-5-(benzyloxy)-5-oxopentanoic acid

Glutamic acid (20 g, 0.14 mol, 1 equiv), BnOH (21.1 mls, 0.20 moles, 1.5 equiv) were dissolved in of toluene (30 ml) with stirring in a three necked RB flask. To the resultant mixture methanesulphonic acid (10.6 ml, 0.16 mol, 1.2 equiv) was added slowly whilst maintaining the temperature of the mixture at 45° C. Stirring was continued at this temperature for 2 hrs following which the mixture was cooled to 30° C. and stirred for an additional 4 hrs. Water (50 ml) was then added to the mixture and the organic phase was separated. To the aqueous phase ethanol (30 ml) was added followed by cold aq. ammonia to obtain a pH of 6.5-7. At this point a thick white precipitate was formed which could either be heated to 60° C. and stirred for 2 hrs to improve the crystallinity and then cooled to 5-10° C. or filtered at this point and washed with ethanol (2×20 ml) and water (3×20 ml). The product is then allowed to dry and used without further purification (3.45 g, 21%).

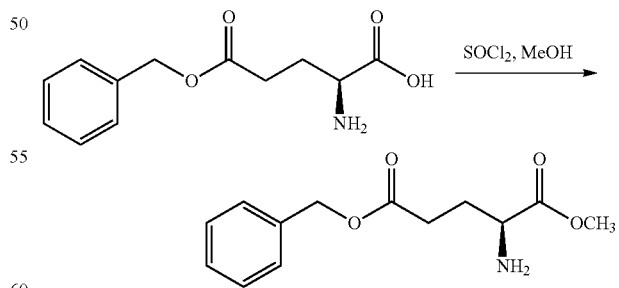

Synthesis of (S)-5-benzyl 1-methyl
2-aminopentanedioate

To methanol (50 ml) γ-benzyl glutamic acid (2.10 g, 8.86 mmol, 1 equiv) was added and the solution cooled to 0° C.

Thionyl chloride (0.76 ml, 10.6 mmol, 1.2 equiv) was then added dropwise at a rate that maintained the temperature at 0-5° C. The mixture was allowed to warm to room temperature and stirred for a further 18 hrs. The solvent was removed in vacuo to afford γ-benzylmethylglutamate as a pale yellow oil which solidified on standing (2.74 g, 48%).

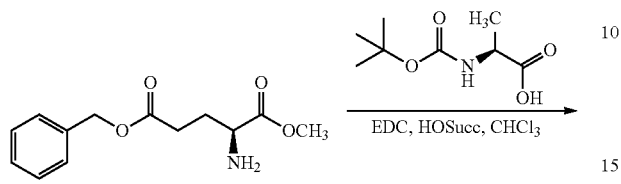

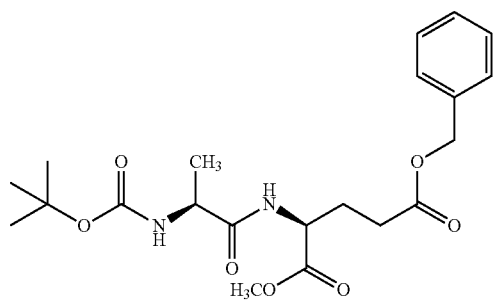

Synthesis of (S)-5-benzyl 1-methyl 2-((S)-2-((tert-butoxycarbonyl)amino) propanamido)pentanedioate The methyl glutamate (3.06 g, 10 mmol) was dissolved in CHCl$_3$ (20 ml). To this TEA (4.8 ml, 28.7 mmol) was added at 0° C. and the reaction mixture stirred for 15-30 mins. N-Boc alanine (2.29 g, 10 mmol) in CHCl$_3$ (20 ml) and EDC (2.31 g, 10 mmol) were added and the resultant mixture and stirred for 12 hrs. Subsequently the mixture was filtered and the residue washed with CHCl$_3$ (30 ml). The combined organics were washed sequentially with 5% NaHCO$_3$ (20 ml), 5% HCl (20 ml) and distilled water (20 ml). The organic layer was dried over anhydrous Na$_2$SO$_4$, filtered and evaporated to yield the peptide. Dark yellow viscous oil, 2.604 g, 38%; $^1$H NMR $\delta_H$: 1.37 (t, 3H), 1.42 (s, 9H), 2.03 (m, 1H), 2.23 (m, 1H), 2.41 (m, 2H), 3.75 (s, 3H), 4.20 (q, 1H), 4.58 (t, 1H), 5.10 (s, 2H), 7.35 (m, 5H); $^{13}$C NMR (75 MHz) $\delta_C$ ppm: 14.63 (C—CH$_3$), 27.98 (C—(CH$_3$)$_3$), 26.89 (CH—CH$_2$), 29.96 (CH$_2$—CH$_2$), 51.97(CH—), 52.42 (O—CH$_3$), 53.19 (CH—), 64.97 (CH$_2$—Bn), 127.03-128.56 (Benzyl), 172.81(O—C=O—NH), 173.26 (C=O—NH), 175.96 (C=O—OCH3), 176.28(C=O—OCH$_2$Bn); ESI-MS calculated for C$_{21}$H$_{30}$N$_2$O$_7$Na, 445.1951 obtained M+Na 445.1929.

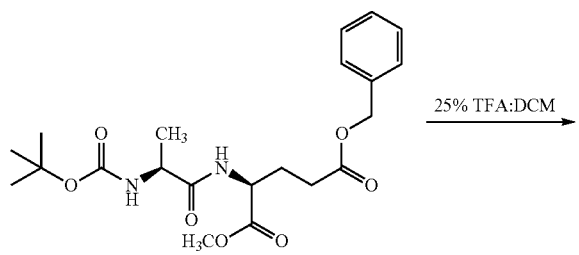

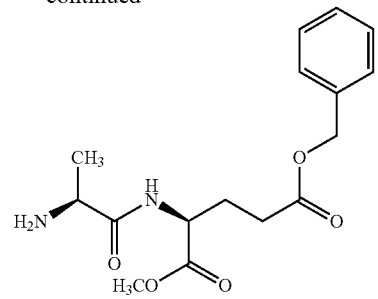

Synthesis of (S)-5-benzyl 1-methyl 2-((S)-2-aminopropanamido)pentanedioate

The above dipeptide (0.661 g, 1.83 mmol) was dissolved in dichloromethane (10 ml) and cooled to 0° C. Trifluoroacetic acid (2.5 ml) was added and the mixture stirred at 0° C. for 10 mins and allowed to warm to room temperature and stirred for a further 40 mins. The solvents were removed in vacuo to give a brown residue. This was re-dissolved in DCM and washed with cold saturated NaHCO$_3$ (10 ml). The organic layer was dried with Na$_2$SO$_4$ and the solvent removed in vacuo to give the free amine which was used immediately for the next step (100%).

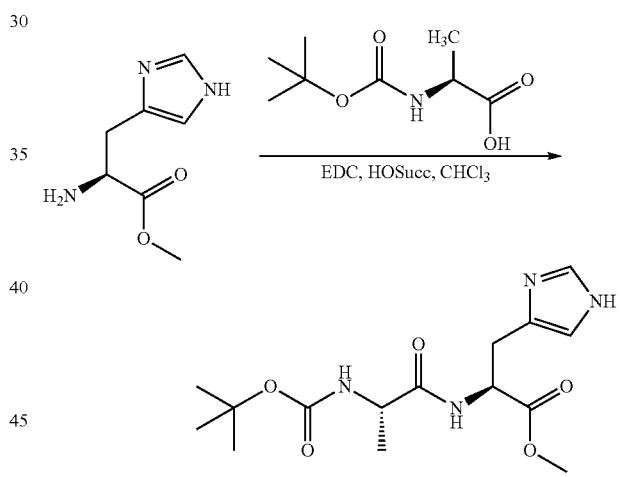

Reaction Conditions: Boc$_2$O, HOSucc, TEA, DMAP

Synthesis of (S)-methyl 2-((S)-2-((tert-butoxycarbonyl)amino)propanamido)-3-(1H-imidazol-4-yl)propanoate To a solution of di-tert-butyl dicarbonate (6.86 mmol, 1.4 equiv) dissolved in 50 ml of dry dichloromethane were added consecutively N-terminal-protected amino acid (Boc-alanine, 4.9 mmol, 1 equiv), N-hydroxysuccinimide (4.9 mmol, 1 equiv), triethylamine (9.8 mmol, 2 equiv) and DMAP (2.45 mmol, 0.5 equiv). After 3½ hours the C-terminal-protected amino acid (histidine methyl ester, 5.88 mmol, 1.2 equiv) was added and the reaction allowed to proceed overnight. Dichloromethane (50 ml) was added and the resultant solution was washed with water (35 ml), 2% HCl (35 ml), a saturated NaHCO$_3$ solution (35 ml) and water (25 ml) dried over MgSO$_4$ and evaporated to give the peptide. Clear viscous oil, 1.85 g, 40.27%; [α]$^{23°}$ CHCl$_3$=+9 (c=1); ν$_{max}$(film)/cm$^{-1}$:

3401., 1742., 1684; $R_f$(CHCl$_3$—CH$_3$OH 9:1); $^1$H NMR $\delta_H$: 1.35(d, 3H), 1.45(s, 9H), 2.80(s, 1H), 3.05(t, 1H, J=5.6 Hz), 3.15(t, 1H, J=5.6 Hz), 3.70(s, 3H), 4.25(t, 1H) 4.82(q, 1H, J=4.8 and 5.2 Hz), 7.15(s, 1H, imidazole-H), 8.00(s, 1H, imidazole-H); $^{13}$C NMR (75 MHz) $\delta_C$ ppm: 18.28, (C—CH$_3$), 27.82, 31.17, 39.58, 51.84, (O—CH$_3$) 51.98, 52.35, 136.84, 138.44, 146.77, (imidazole C) 169.09, 171.58. (C=O); ESI MS calculated for C$_{15}$H$_{25}$N$_4$O$_5$, 341.1825 found M+H, 341.1819.

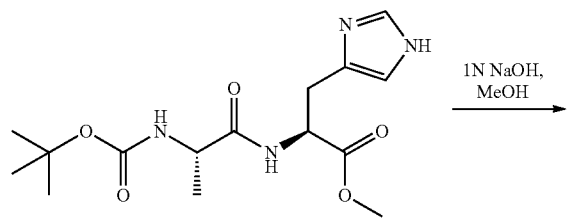

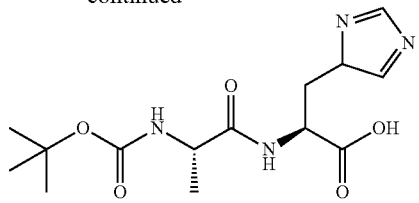

Synthesis of (2S)-2-((S)-2-((tert-butoxycarbonyl)amino)propanamido)-3-(4H-imidazol-4-yl)propanoic acid The dipeptide (Boc-alanylhistidinyl methyl ester, 1 g, 2.87 mmol) was dissolved in a mixture of methanol (3 ml) and 1M NaOH (3 ml) and stirred at RT for 1 hrs. To this water (6 ml) was added; extracted with ether (6 ml). The aqueous phase was acidified to pH 3 with 3M citric acid. The resultant oil was extracted with ethyl acetate (2×10 ml) and the combined extracts were dried over Na$_2$SO$_4$. Removal of the solvent in vacuo gave the product as a white solid (0.31 g, 33%).

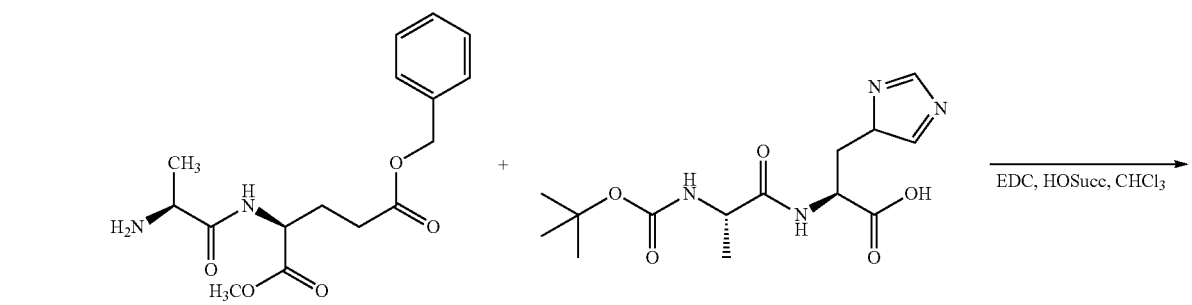

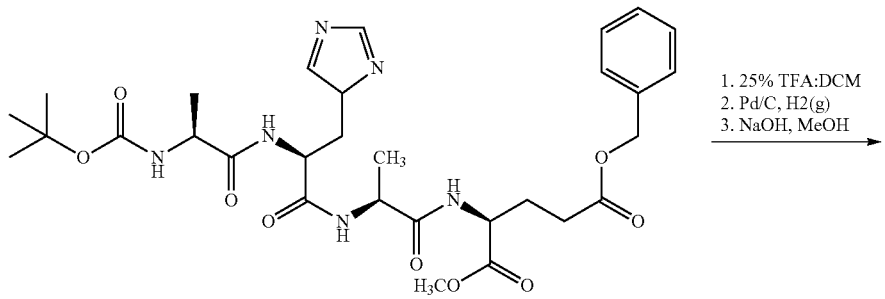

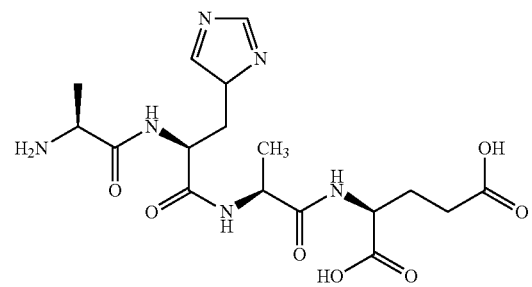

Synthesis of (2S)-2-((2S)-2-((2S)-2-((S)-2-amino-propanamido)-3-(4H-imidazol-4-yl)propanamido) propanamido)pentanedioic acid (AlaHisAlaGlu)

Alanyl-γ-benzylmethylglutamate (0.1 g, 0.31 mmol, 1 equiv) was dissolved in CHCl$_3$ (5 ml). To this TEA (0.124 ml, 0.88 mmol, 2.84 equiv) was added at 0° C. and the reaction mixture stirred for 30 mins at RT. To this solution N-Boc-AlanylHistidine (0.1 g, 0.31 mmol, 1 equiv) in CHCl$_3$ (50 ml) and EDC (0.059 g, 0.31 mmol, 1 equiv) were added and the mixture stirred at RT for 12 hrs. Following this the mixture was filtered and the residue was washed with CHCl$_3$ (10 ml) and the combined organics washed with 5% NaHCO$_3$ (10 ml), 5% HCl (10 ml) and distilled water (10 ml). The organic layer was dried over anhydrous Na$_2$SO$_4$, filtered and evaporated to yield the peptide. The peptide was then dissolved in a mixture of methanol (3 ml) and 1M NaOH (3 ml) and stirred at RT for 1 hour. To this water (6 ml) was added; extracted with ether (6 ml). The aqueous phase was acidified to pH 3 with 3M citric acid. The resultant oil was extracted with ethyl acetate (2×10 ml) The combined extracts were dried over Na$_2$SO$_4$ to yield the free acid. This was then dissolved in ethanol and Pd/C added to it. The reaction mixture was then placed in a hydrogenator and shaken overnight. The mixture was filtered through celite and the filtrate was collected. The solvent was removed in vacuo and the residue dissolved in dichloromethane (5 ml) and cooled to 0° C. Trifluoroacetic acid (1.25 ml) was added and the mixture stirred at 0° C. for 10 mins and allowed to warm to room temperature and stirred for a further 40 mins. The solvents were removed in vacuo. This was re-dissolved in DCM and washed with cold saturated NaHCO$_3$ (10 ml). The organic layer was dried with Na$_2$SO$_4$ and the solvent removed in vacuo to give the deprotected peptide. $^1$H NMR $\delta_H$: 1.30 (d, 3H), 1.41 (d, 3H), 1.90 (m, 1H), 2.11 (m, 1H), 2.39 (dd, 2H), 3.15 (dddd, 2H), 3.99 (q, 1H), 4.24 (q, 1H), 4.28 (dd, 1H), 4.65 (t, 1H), 7.24 (s, 1H), 8.55 (d, 1H); $^{13}$C NMR (150 MHz) $\delta_C$ ppm: 16.44 (—CH$_3$), 16.45 (—CH$_3$), 26.08 (CH$_2$CH$_2$CO$_2$H), 30.10 (—CH$_2$CO$_2$H), 26.39 (CH$_2$-Im), 48.84 (NH$_2$—CH—CH$_3$), 49.70 (NH—CH—CH$_3$), 52.43 (CH—C$_2$H$_4$CO$_2$H), 52.70 (CH—CH$_2$Im), 115.36 (Im), 117.45 (ImCH), 133.63 (Im), 170.61 (CONH), 170.87 (CONH), 174.52 (CONH), 175.64 (CO$_2$H), 177.32 (CO$_2$H).

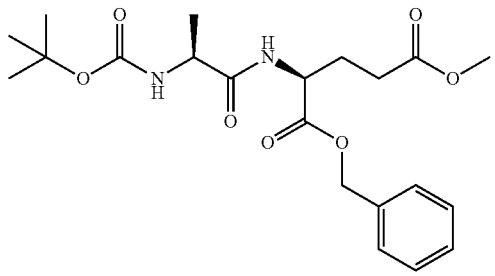 [SMILES: COC(=O)CC[C@H](NC(=O)[C@H](C)NC(=O)OC(C)(C)C)C(=O)OCc1ccccc1]

Synthesis of (S)-1-benzyl 5-methyl 2-((S)-2-((tert-butoxycarbonyl)amino) propanamido)pentanedioate γ-Benzyl glutamic acid methyl ester (3.06 g, 10 mmol) was dissolved in CHCl$_3$ (20 ml). To this triethylamine (4.82 ml, 28.7 mmol) was added at 0° C. and the reaction mixture stirred for 15-30 mins. N-Boc alanine (2.29 g, 10 mmol) in CHCl$_3$ (20 ml) and EDC (2.31 g, 10 mmol) were added and the reaction stirred for 12 hrs. The mixture was filtered and the residue was washed with CHCl$_3$ (30 ml) and the washings were added to the filtrate. The filtrate was washed with 5% NaHCO$_3$ (20 ml), 5% HCl (20 ml) and distilled water (20 ml). The organic layer was dried over anhydrous Na$_2$SO$_4$, filtered and evaporated to yield the peptide. Light brown viscous oil, 2.604 g, 38.1%; $^1$H NMR $\delta_H$: 1.37 (t, 3H), 1.42 (s, 9H), 2.03 (m, 1H), 2.23 (m, 1H), 2.41 (m, 2H), 3.75 (s, 3H), 4.20 (q, 1H), 4.58 (t, 1H), 5.10 (s, 2H), 7.35 (m, 5H); $^{13}$C NMR (75 MHz) $\delta_C$ ppm:14.63 (C—CH$_3$), 27.98 (C—(CH$_3$)$_3$), 26.89 (CH—CH$_2$), 29.96 (CH$_2$—CH$_2$),51.97(CH—), 52.42 (O—CH$_3$), 53.19 (CH—), 64.97 (CH$_2$—Bn), 127.03-128.56 (benzyl), 172.81(O—C=O—NH), 173.26 (C=O—NH), 175.96 (C=O—OCH3), 176.28(C=O—OCH$_2$Bn); ESI-MS calculated for C$_{21}$H$_{30}$N$_2$O$_7$Na, 445.1951 obtained M+Na 445.1929.

Example 2

Catalytic Oxidation of Methane to Methanol Using AlaHisAlaGlu Copper Catalyst 0.15 mM (0.00078 g) of peptide was dissolved in 10 cm$^3$ of D$_2$O and 0.12 mM (CuCl$_2$.2H$_2$O) was added to at room temperature and atmospheric pressure at pH 7. After 10 mins the solution had changed color (light blue for peptide AlaHis-AlaGlu). The reaction mixture was allowed to stir for 1 hr after which a sample was removed and analyzed using NMR ($^1$H). Subsequently O$_2$ (gas) was bubbled through the solution for 1 hr and a sample was removed and analyzed by NMR. Methane was then introduced to the reaction flask by via simultaneously bubbling into the mixture. The bubbling of methane was continued for a further 1 hr. Analysis of an aliquot of the reaction mixture was carried utilizing NMR. The reaction was continued for a further one hour after which the reaction was terminated.

FIG. 1 shows a $^1$HNMR spectra of a Cu(II)(AlaHisAlaGlu) catalyst with oxygen. In comparing the $^1$HNMR spectra of the Cu(II)(AlaHisAlaGlu) catalyst with the $^1$HNMR spectra of the free peptide, there is significant line broadening of the imidazole aromatic protons and CH$_2$ on the side chain of histidine, as well as line broadening of the CH$_2$'s of the glutamic acid side chain. Furthermore there is random shifting of other signals either up field or downfield which confirms the generation of the Cu(II)(AlaHisAlaGlu) catalyst.

Figure 2:
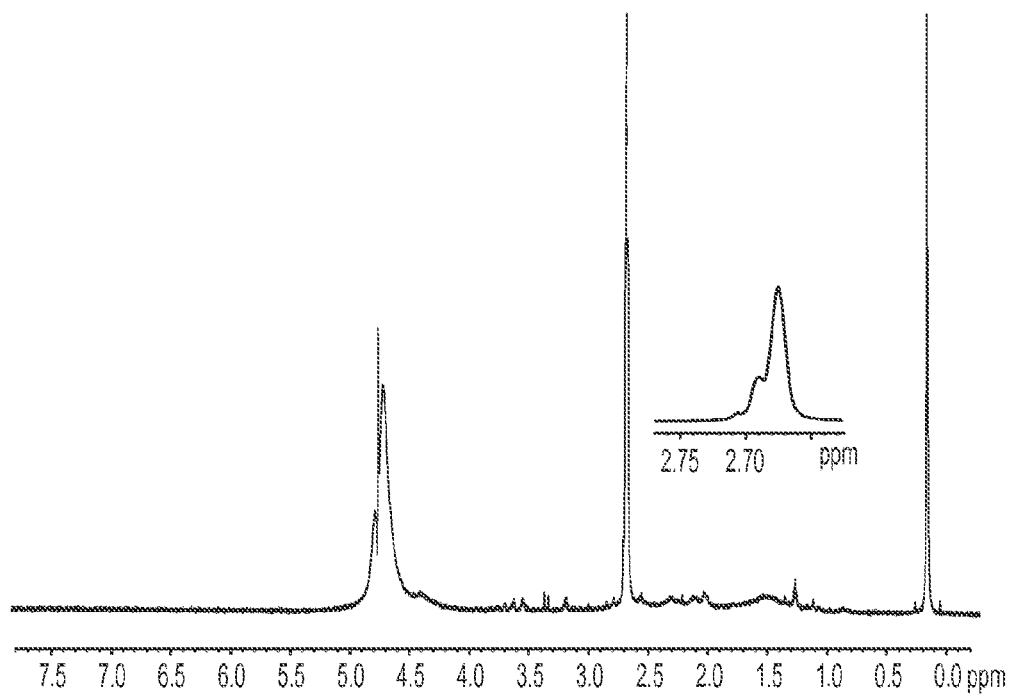
FIG. 2 shows a representative $^1$HNMR spectra of a Cu(II)(AlaHisAlaGlu) catalyst with oxygen, methane and methanol.
Figure 3:
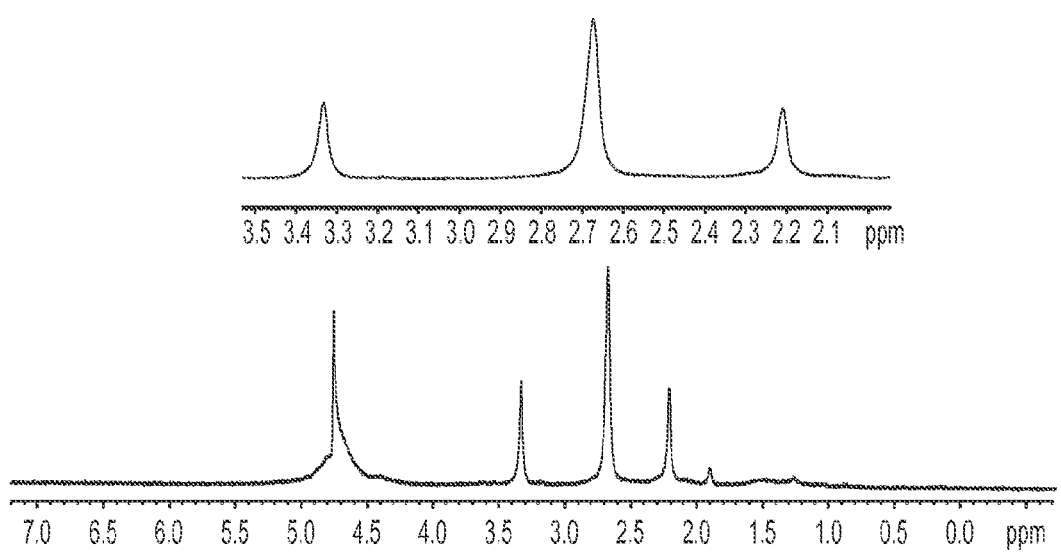
FIG. 3 shows a representative $^1$HNMR spectra sectional view of a Cu(II)(AlaHisAlaGlu) catalyst with oxygen, methane and methanol.

FIG. 2 and FIG. 3 show the catalytic oxidation of a methane to methanol using Cu(II)(AlaHisAlaGlu) catalyst in the presence of oxygen. In comparing the 1HNMR spectra of Cu(II) (AlaHisAlaGlu) catalyst with Cu(II)(AlaHisAlaGlu) catalyst in the presence of oxygen there was not a notable difference. On introduction of the methane a large peak at 2.67 ppm was seen which appeared to be a poorly resolved triplet. On repeating the NMR of this reaction mixture the signal separated into three distinct singlets at 2.20, 2.70 and 3.35 ppm respectively. The 3.35 ppm singlet is representative of methanol formation which confirms the catalytic oxidation of methane to methanol using a Cu(II)(AlaHisAlaGlu) catalyst in the presence of oxygen.

Figure 4:
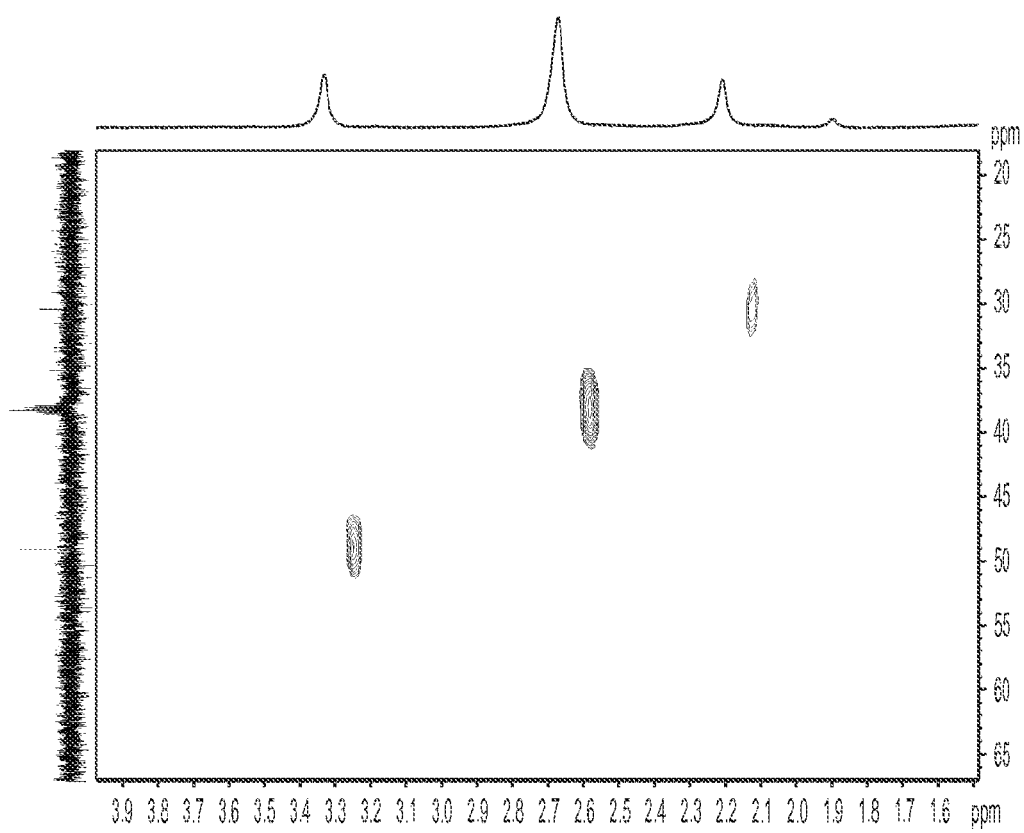
FIG. 4 shows a representative HSQC spectra of a Cu(II)(AlaHisAlaGlu) catalyst with oxygen, methane and methanol.

FIG. 4 shows a HSQC spectra which confirms the catalytic oxidation of methane to methanol using a Cu(II)(AlaHisAla-Glu) catalyst in the presence of oxygen. The HSQC spectra shows a contour corresponding at 3.35 ppm on the 1HNMR spectra and 48 ppm on the 13CNMR spectra which corresponds with methanol formation which confirms the catalytic oxidation of methane to methanol using a Cu(II)(AlaHisAla-Glu) catalyst in the presence of oxygen.

Figure 6A:
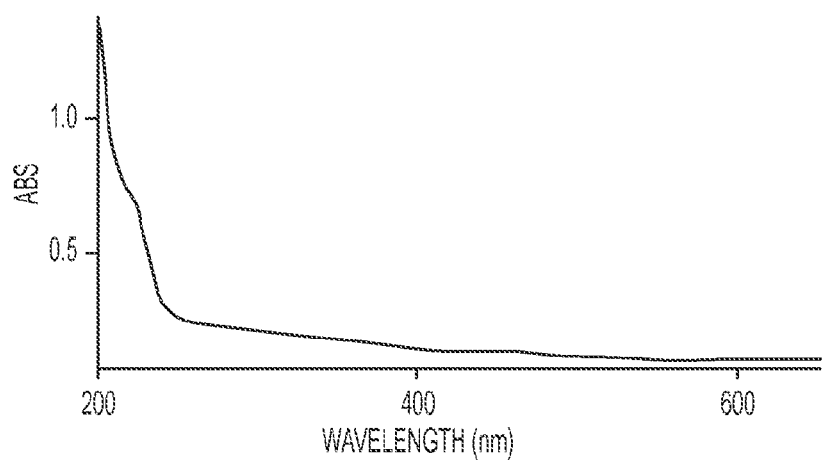
FIGS. 6A, 6B and 6C show a representative UV-VIS spectra of a Cu(II)(AlaHisAlaGlu) catalyst with oxygen.
Figure 6B:
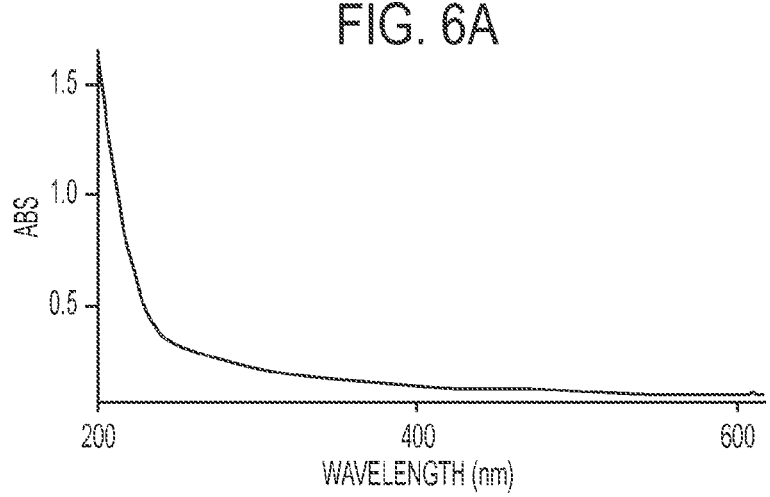
Figure 6C:
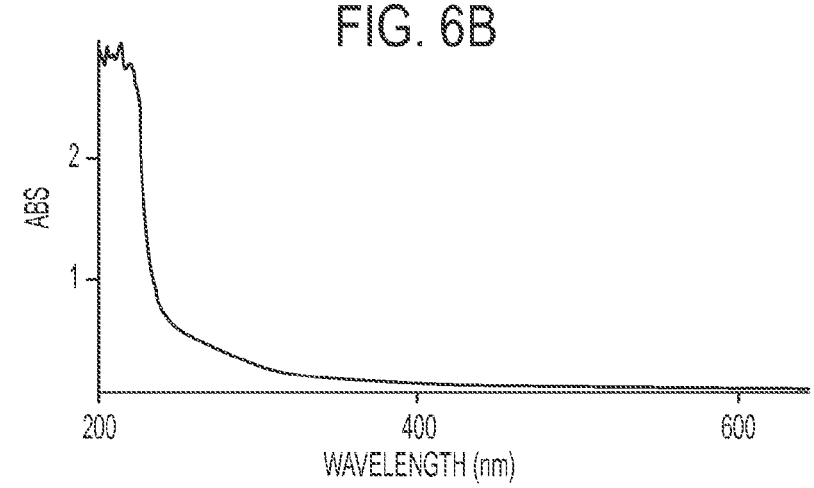

FIGS. 6A, 6B and 6C show UV-VIS spectra which confirms the generation of a Cu(II)(AlaHisAlaGlu) catalyst in the

Example 3

Synthesis of AlaMetAspTrp

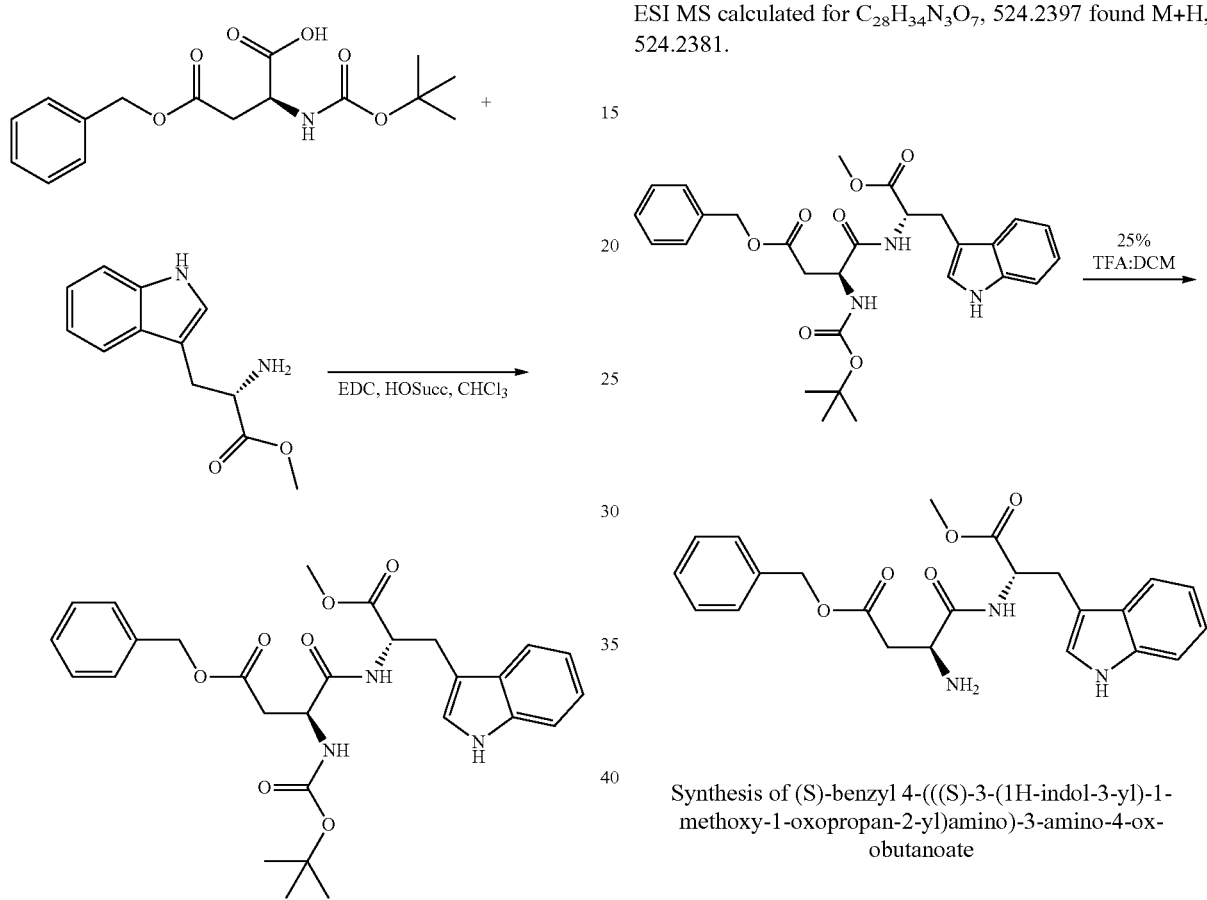

Reaction Conditions: Boc$_2$O, HOSucc, TEA, DMAP

Synthesis of (S)-benzyl 4-(((S)-3-(1H-indol-3-yl)-1-methoxy-1-oxopropan-2-yl)amino)-3-((tert-butoxycarbonyl)amino)-4-oxobutanoate To a solution of di-tert-butyl dicarbonate (4.2 mmol, 1.4 equiv) dissolved in 50 ml of dry dichloromethane were added consecutively N-terminal-protected amino acid (Boc-β-benzyl aspartic acid, 3 mmol, 1 equiv), N-hydroxysuccinimide (3 mmol, 1 equiv), triethylamine (6 mmol, 2 equiv) and DMAP (1.5 mmol, 0.5 equiv). After 3½ hours the C-terminal-protected amino acid (tryptophan methyl ester, 3.6 mmol, 1.2 equiv) was added and the reaction allowed to proceed overnight. The mixture was diluted with dichloromethane (50 ml) and the resultant solution was washed with water (35 ml), 2% HCl (35 ml), a saturated NaHCO$_3$ solution (35 ml) and water (30 ml), dried over MgSO$_4$ and evaporated to give the peptide. Clear dark yellow viscous oil, 1.56 g, 83%; [α]$^{23°}$ in MeOH=+4.0 (c=1); ν$_{max}$(film)/cm$^{-1}$: 3382.8, 3057.1, 2977.8, 1738.7, 1619.7; R$_f$(CHCl$_3$—CH$_3$OH 9:1); $^1$H NMR δ$_H$: 1.35 ppm (s, 9H), 2.76 ppm (dd, 1H, J=6.4 and 5.2 Hz), 2.85 ppm (dd, 1H, J=4.8 and 4 Hz), 3.24 ppm (s, 1H), 3.49 ppm (s, 3H), 4.60 ppm (t, 1H), 4.85 ppm (t, 1H), 5.0 ppm (s, 2H), 6.88-7.60 ppm (arom, 9H); $^{13}$C NMR (75 MHz) CDCl$_3$ δ$_C$: 27.23, 27.38, 27.50, 27.78, 36.57, 51.72, 52.81, 54.05, 66.29, 79.40, 81.92, 111.13, 117.89, 118.07, 121.44, 123.04, 127.03, 127.21, 127.75, 127.84, 128.11, 128.15, 135.10, 135.12, 155.10, (arom C) 170.35, 171.57, 171.70(C=O); ESI MS calculated for C$_{28}$H$_{34}$N$_3$O$_7$, 524.2397 found M+H, 524.2381.

Synthesis of (S)-benzyl 4-(((S)-3-(1H-indol-3-yl)-1-methoxy-1-oxopropan-2-yl)amino)-3-amino-4-oxobutanoate In a 50 ml flask, the protected amine was (Bocaspartyl(Bn) tryptophan methyl ester, (0.661 g, 1.83 mmol) was dissolved in dichloromethane (10 ml) and cooled to 0° C. To the resultant solution trifluoroacetic acid (2.5 ml) was added and the mixture stirred at 0° C. for 10 mins and allowed to warm to room temperature for 40 mins. The solvents were then evaporated in vacuo to give a dark brown residue. This was re-dissolved in DCM (25 ml) and washed with cold saturated NaHCO$_3$ solution (10 ml). The organic layer was dried over Na$_2$SO$_4$ and the solvent removed in vacuo to afford the title compound. Clear brown viscous oil, 0.43 g, 82%; [α]$^{23°}$ in DCM=+6 (c=1); R$_f$(CHCl$_3$—CH$_3$OH 9:1); $^1$H NMR (600 MHz) δ$_H$: 2.75 ppm(dd, 1H), 2.85 ppm(dd, 1H), 3.10 ppm (dd, 1H), 3.22 ppm(dd, 1H), 3.60 ppm(s, 3H), 4.40 ppm(t, 1H), 4.79 ppm(t, 1H), 5.25 ppm(s, 2H); $^{13}$C NMR δ$_C$: 27.60, 34.47, 46.72, 50.08, 52.98, 68.19, 108.81, 109.46, 111.68, 118.12, 119.12, 120.86, 126.97, 128.36, 128.47, 128.71, 128.86, 134.32, 136.28, (arom C) 159.93, 167.59, 170.60, 171.91 (C=O); ESI MS calculated for C$_{23}$H$_{26}$N$_3$O$_5$, 424.1872 found M+H, 424.1833.

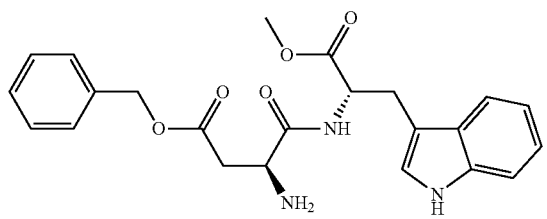 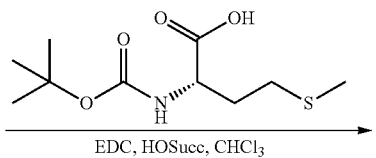

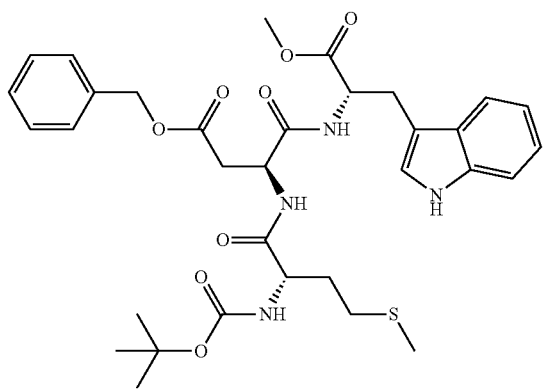

Reaction Conditions: Boc$_2$O, HOSucc, TEA, DMAP

Synthesis of 6S,9S,12S)-methyl 12-((1H-indol-3-yl) methyl)-9-(2-(benzyloxy)-2-oxoethyl)-2,2-dimethyl-6-(2-(methylthio)ethyl)-4,7,10-trioxo-3-oxa-5,8,11-triazatridecan-13-oate To a solution of di-tert-butyl dicarbonate (8.25 mmol, 1.4 equiv) dissolved in 50 ml of dry dichloromethane were added consecutively N-terminal-protected amino acid (Bocmethionine, 5.90 mmol, 1 equiv), N-hydroxysuccinimide (5.90 mmol, 1 equiv), triethylamine (11.7 mmol, 2 equiv) and DMAP (2.95 mmol, 0.5 equiv). After 3½ hours the C-terminal-protected amino acid (Asp(BnTrpOMe, 7.02 mmol, 1.2 equiv) was added and the reaction allowed to proceed for 18 hrs. The mixture was diluted with dichloromethane (50 ml) and the solution was washed with water (50 ml), 2% HCl (50 ml), a saturated NaHCO$_3$ solution (50 ml) and water (20 ml) dried over MgSO$_4$ and evaporated to give the peptide. Clear light brown viscous oil, 3.33 g, 86%: $[\alpha]^{23°}$ in DCM=+3 (c=1); $^1$H NMR (600 MHz) $\delta_H$: 1.40 ppm (s, 9H), 1.55 ppm (s, 3H), 1.70 ppm (q, 2H), 2.08 ppm (s, 3H), 2.55 ppm (dd, 1H), 2.70 ppm (dd, 1H), 3.05 ppm (dd, 1H), 3.30 ppm (dd, 1H), 3.66 ppm (s, 3H), 4.25 ppm (t, 1H), 4.55 ppm (t, 1H), 4.85 ppm (t, 1H), 5.39 ppm (s, 2H), 5.64 ppm (dd, 1H), 6.90-7.60 ppm (arom) 10H; $^{13}$CNMR (150 MHz): 14.11, 28.02, 28.20, 28.30, 29.36, 29.70, 31.59, 31.79, 36.30, 52.32, 52.73, 53.09, 66.80, 109.69, 111.26, 117.19, 118.58, 119.6, 122.1, 126.7, 126.9, 127.5, 128.2, 128.34, 128.45, 134.46, 134.47, (arom) 169.04, 171.87, 192.38(C=O); ESI MS calculated for C$_{33}$H$_{42}$N$_4$O$_8$SNa, 677.2621 found M+Na, 677.2616.

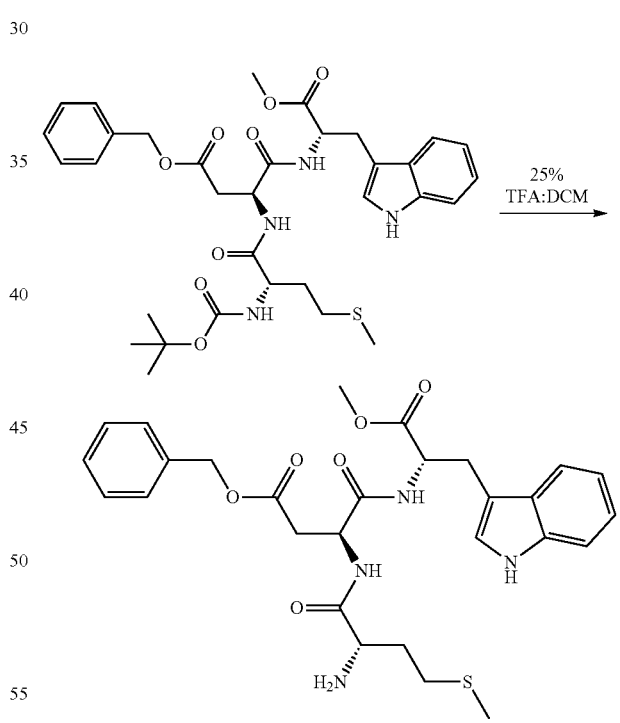

Synthesis of (S)-benzyl 4-(((S)-3-(1H-indol-3-yl)-1-methoxy-1-oxopropan-2-yl)amino)-3-((S)-2-amino-4-(methylthio)butanamido)-4-oxobutanoate In a 50 ml flask, the protected amine (BocMetAsp(Bn) TrpOMe, 1.53 mmol, 1 g) was dissolved in dichloromethane (10 ml) and cooled to 0° C. Trifluoroacetic acid (2.5 ml) was added and the mixture stirred at 0° C. for 10 mins and allowed to warm to room temperature for 40 mins. The solvents were the evaporated in vacuo to give a dark brown residue. This was re-dissolved in DCM and washed with cold saturated NaHCO$_3$ solution (10 ml). The organic layer was dried with Na$_2$SO$_4$ and the solvent removed in vacuo to give the product. Clear Brown viscous oil, 0.58 g, 68.4%: $[\alpha]^{23°}$ in DCM=+6 (c=1); $^1$H NMR (300 MHz) $\delta_H$(ppm): 2.01 (s, 3H), 2.57 (dd, 1H, J=8.7 and 9 Hz), 2.90 (ddd, 1H, J=3.6, 3.6 and 3.9 Hz), 3.29 (d, 2H), 3.65 (s, 3H), 4.15 (dt, 1H), 4.23 (dt, 1H), 4.86 (dt, 1H, J=2.4 and 3.6 Hz), 5.09 (s, 2H), 5.30 (s, 2H), 6.85-7.40 (10H, arom), 7.60 (dd, 1H), 7.85 (d, 1H), 8.40 (ad, 1H); $^{13}$C NMR (75 MHz) $\delta_C$: 14.16(S—CH$_3$), 26.97, 27.62, 27.73, 28.62, 51.9 (O—CH$_3$), 52.00, 52.60, 52.78, 66.74(O—CH$_2$), 108.21, 110.95, 117.98, 118.78, 121.27, 121.39, 123.05, 126.56, 126.70, 127.69, 127.87, 127.97, 134.34, 135.52, (arom C), 167.65, 169.99, 170.12, 171.90 (C=O); ESI MS calculated for C$_{28}$H$_{35}$N$_4$O$_6$S, 555.2277 found M+H, 555.2174.

mmol, 1 equiv), triethylamine (5.6 mmol, 2 equiv) and DMAP (1.41 mmol, 0.5 equiv). After 3½ hours the C-terminal-protected amino acid (MetAsp(BnTrpOMe, 3.38 mmol, 1.2 equiv) was added and the reaction allowed to proceed overnight. Chloroform or dichloromethane was added and the solution was washed with water (35 ml), 2% HCl (35 ml), a saturated NaHCO$_3$ solution (35 ml) and water dried with MgSO$_4$ and evaporated to give the peptide. Clear viscous oil, 1.92 g, 93.8%; $^1$H NMR (300 MHz) $\delta_H$: 1.45 (12H, s), 1.70 (3H, d), 1.98 (1H, m), 2.1 (1H, d), 2.55 (2H, q), 2.75 (2H, s), 3.30 (3H, q), 3.70 (3H, tdt), 4.20 (2H,q), 4.47(1H, dd), 4.69 (1H, s), 5.02 (2H, d), 5.19 (2H, dd), 7.10 (8H, m) 7.5 (4H, t); $^{13}$CNMR (75 MHz): 14.15 (S—CH$_3$), 15.43 (CH$_3$—C), 25.45 ((CH$_3$)$_3$—O—C=O), 27.40 ((CH$_3$)$_3$—O—C=O), 27.82 ((CH$_3$)$_3$—O—C=O), 28.31 (CH$_2$—In), 29.30 (CH$_2$—

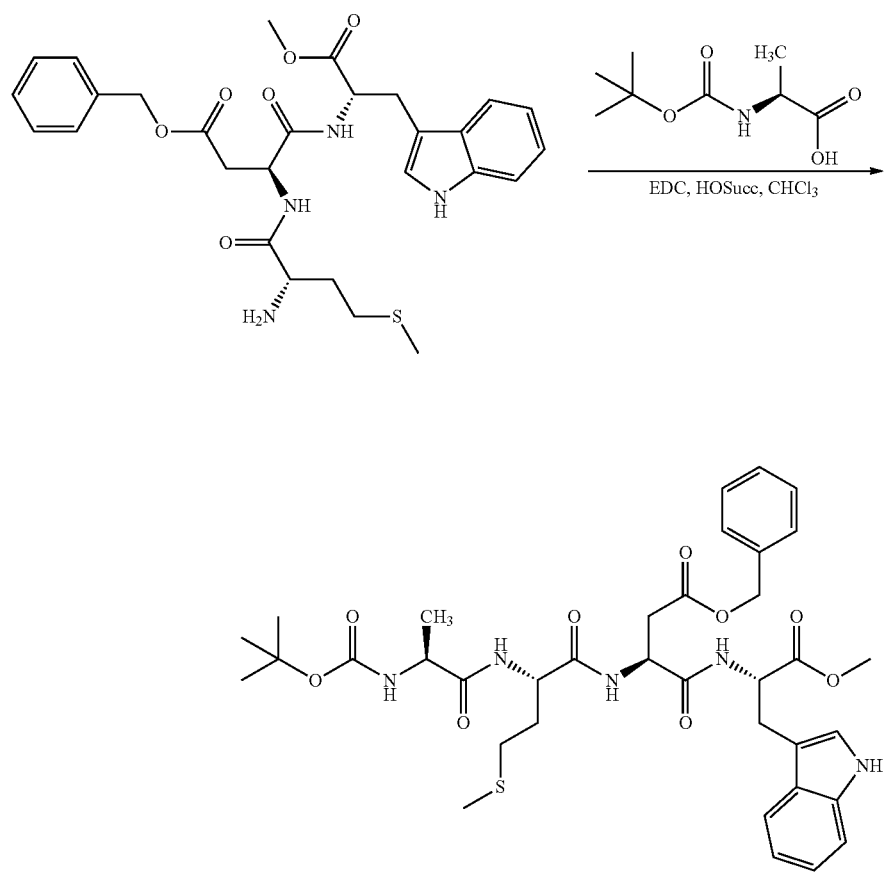 [SMILES: COC(=O)[C@H](Cc1c[nH]c2ccccc12)NC(=O)[C@H](CC(=O)OCc1ccccc1)NC(=O)[C@@H](N)CCSC ; C[C@H](NC(=O)OC(C)(C)C)C(=O)O ; COC(=O)[C@H](Cc1c[nH]c2ccccc12)NC(=O)[C@H](CC(=O)OCc1ccccc1)NC(=O)[C@H](CCSC)NC(=O)[C@H](C)NC(=O)OC(C)(C)C]

Reaction Conditions: Boc$_2$O, HOSucc, TEA, DMAP

Synthesis of (6S,9S,12S,15S)-methyl 15-((1H-indol-3-yl)methyl)-12-(2-(benzyloxy)-2-oxoethyl)-2,2,6-trimethyl-9-(2-(methylthio)ethyl)-4,7,10,13-tetraoxo-3-oxa-5,8,11,14-tetraazahexadecan-16-oate To a solution of di-tert-butyl dicarbonate (3.9 mmol, 1.4 equiv) dissolved in 50 ml of dry dichloromethane were added consecutively N-terminal-protected amino acid (Boc-Alanine, 2.82 mmol, 1 equiv), N-hydroxysuccinimide (2.82

S), 31.78 (CH$_2$—CH$_2$S), 37.08 (CH$_2$—C=O), 51.06 (CH$_3$—COO), 53.46 (CH—CH$_3$), 55.54 (CH—CH$_2$), 61.48 (CH—CH$_2$), 61.62(CH—CH$_2$), 66.65 (O—CH$_2$—Bn), 87.84((CH$_3$)$_3$—O—C=O), 109.51 (In), 111.40(In), 118.69 (In), 119.44(In), 122.01 (In), 123.19(In), 126.95(Bn), 127.06 (Bn), 127.47(In), 127.79(Bn), 128.57(Bn), 128.61 (Bn), 136.18 (Bn), 136.36 (In), 155.42 (O—C=O), 170.34 (C=O), 170.68 (C=O), 171.72 (C=O), 172.37(C=O), 172.72 (C=O); ESI MS calculated for C$_{36}$H$_{47}$N$_5$O$_9$SNa, 748.2992 found M+nNa, 748.3069.

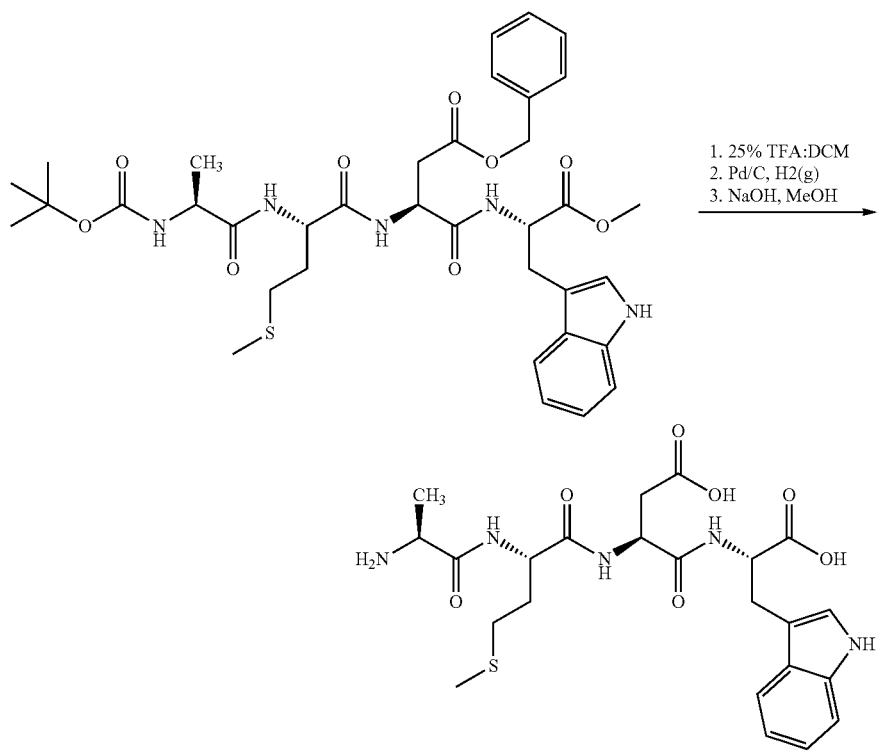

Synthesis of (S)-3-((S)-2-((S)-2-aminopropanamido)-4-(methylthio)butanamido)-4-(((S)-1-carboxy-2-(1H-indol-3-yl)ethyl)amino)-4-oxobutanoic acid (AlaMetAspTrp)

The peptide (1 g) was then dissolved in trifluoroacetic acid (1.25 ml) and the mixture was stirred at 0° C. for 10 mins and allowed to warm to room temperature and stirred for a further 40 mins. The solvents were removed in vacuo. This was re-dissolved in DCM and washed with cold saturated $NaHCO_3$ (10 ml). The organic layer was dried with $Na_2SO_4$ and the solvent removed in vacuo to give the deprotected peptide benzyl4-(3-(1H-indol-3-yl)-1-methoxy-1-oxopropan-2-ylamino)-3-((2S)-2-(2-aminopropanamido)-4-(methylthio)butanamido)-4-oxobutanoate as a dark yellow thick oil. $^1$H NMR 300 MHz $\delta_H$(ppm): 1.49 (3H, t), 2.06 (2H, t), 2.20 (3H, s), 2.69(3H, dt), 2.90(1H, dd), 3.08 (1H, q), 3.29 (1H, td), 3.70 (3H, s) 3.75 (1H, q), 4.09 (1H, t), 4.29 (1H, t), 5.02 (1H, d), 5.10 (1H, t), 6.96 (2H, q), 7.15 (5H, sep), 7.30 (7H, m), 7.60 (1H, d), 8.40 (1H, d), 8.51 (1H, s); $^{13}$C NMR (75 MHz) $\delta_C$: 15.18(S—$CH_3$), 27.83($CH_2$—In), 29.78($CH_2$—S), 30.22($CH_2$—$CH_2$S), 37.60($CH_2$—C=O), 50.74(CH—$CH_3$), 51.15($CH_3$—COO), 51.45 (CH), 52.07(CH—$CH_2$), 55.52(CH—$CH_2$), 66.87(O—$CH_2$—Bn), 108.99(In), 111.30 (In), 118.72(In), 119.52(In), 122.16(In), 123.12(In), 127.02 (Bn), 127.12(Bn), 127.47(In), 128.29(Bn), 128.58(Bn), 128.65(Bn), 136.13(Bn), 136.34(Bn), 166.62(C=O), 166.99 (C=O), 167.29(C=O), 170.38(C=O), 170.67(C=O) ESI-MS calculated for $C_{31}H_{39}N_5O_7SNa$, 648.2470 found M+Na, 648.2482. AlanylMethionylaspartyl(benzyl)tryptophan methyl ester (0.5 g) was then dissolved in ethanol and Pd/C was added. The reaction mixture was then placed in a hydrogenator and shaken overnight. The mixture was filtered through celite and the filtrate was collected. The solvent was removed in vacuo and the residue material was dissolved in dichloromethane (5 ml) and cooled to 0° C. The peptide (0.5 g) was then dissolved in a mixture of methanol (3 ml) and 1M NaOH (3 ml) and stirred at RT for 1 hour. To this water (6 ml) was added and extracted with ether (6 ml). The aqueous phase was acidified to pH 3 with 3M citric acid. The resultant oil was extracted with ethyl acetate (2×10 ml). The combined extracts were dried over $Na_2SO_4$ to yield the free acid. $^1$H NMR (600 MHz) $\delta_H$: 1.40 (3H, t), 1.87 (2H, m), 1.93 (3H, s), 2.34 (2H, q), 2.41 (1H, dd), 2.56 (1H, dd), 3.13 (1H, dd), 3.26 (1H, dd), 3.98 (1H, q), 4.25 (1H, q), 4.43 (1H, t), 4.49 (1H, q), 7.10 (1H, t), 7.14 (1H, s), 7.17 (3H, t), 7.43 (1H, d), 7.61 (1H, d)$^{13}$C NMR (150 MHz)$\delta_C$: 14.08 (S—$CH_3$), 16.36 (—$CH_3$), 29.17 ($CH_2CH_2$—S), 29.69 ($CH_2CH_2$—S), 38.33 ($CH_2$—$CO_2$H), 27.27 ($CH_2$—In), 48.89 (CH—$CH_3$), 52.62 (CHCH$_2$—In), 51.47 (CHCH$_2$CH$_2$—S), 55.58 (CHCH$_2$CO$_2$H), 111.75 (arom), 118.70 (arom), 119.16 (arom), 121.71 (arom), 124.20 (arom), 127.34 (arom), 135.97 (arom), 147.32 (arom), 170.61 (CONH), 171.81 (CONH), 172.57 (CONH), 177.65 (CO$_2$H), 177.90 (CO$_2$H).

Example 4

Generation of AlaMetAspTrp Copper Catalyst 0.15 mM (0.00078 g) of peptide was dissolved in 10 cm$^3$ of $D_2O$ and 0.12 mM ($CuCl_2.2H_2O$) was added to at room temperature and atmospheric pressure at pH 7. After 10 mins the solution had changed color (light purple/pink for peptide AlaMetAspTrp). The reaction mixture was allowed to stir for 1 hr after which a sample was removed and analyzed using NMR ($^1$H). Subsequently $O_2$ (gas) was bubbled through the solution for 1 hr and a sample was removed and analyzed by NMR.

Figure 5:
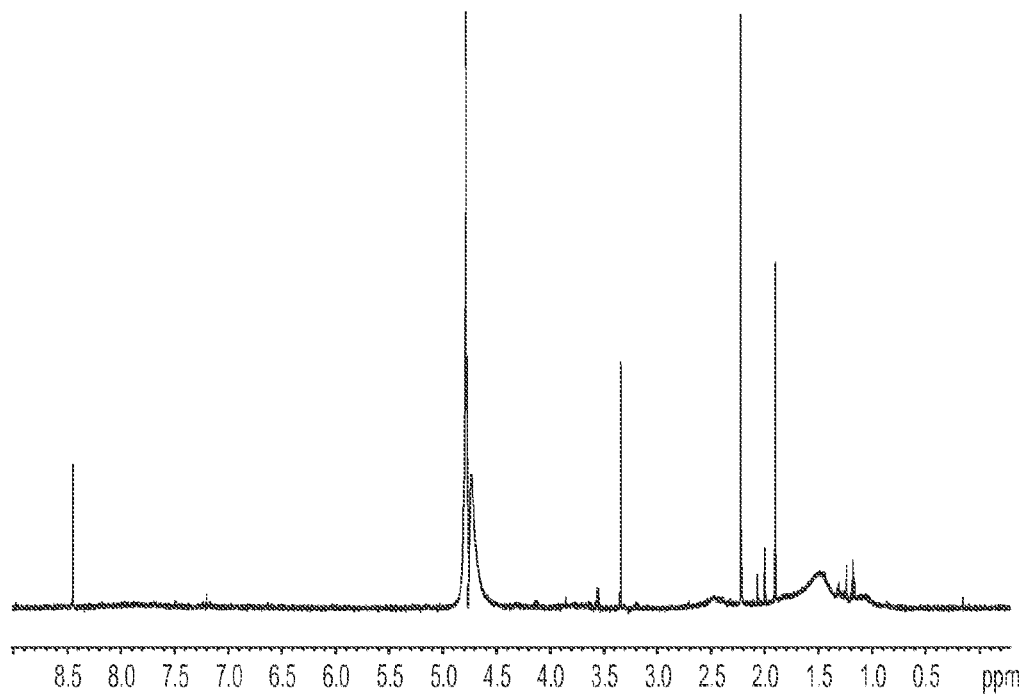
FIG. 5 shows a representative $^1$HNMR spectra of a Cu(II)(AlaMetAspTrp) catalyst with oxygen.

FIG. 5 shows a $^1$HNMR spectra of a Cu(II)(AlaMetAspTrp) catalyst with oxygen. In comparing the 1HNMR spectra of the Cu(II)(AlaMetAspTrp) catalyst with the 1HNMR spectra of the free peptide, there is significant line broadening of the indole aromatic protons and $CH_2$ on the side chain of tryptophan, as well as line broadening of the $CH_2$'s of the aspartic acid side chain. Furthermore there is random shifting of other signals either up field or downfield which confirms the generation of the Cu(II)(AlaMetAspTrp) catalyst.

Figure 7A:
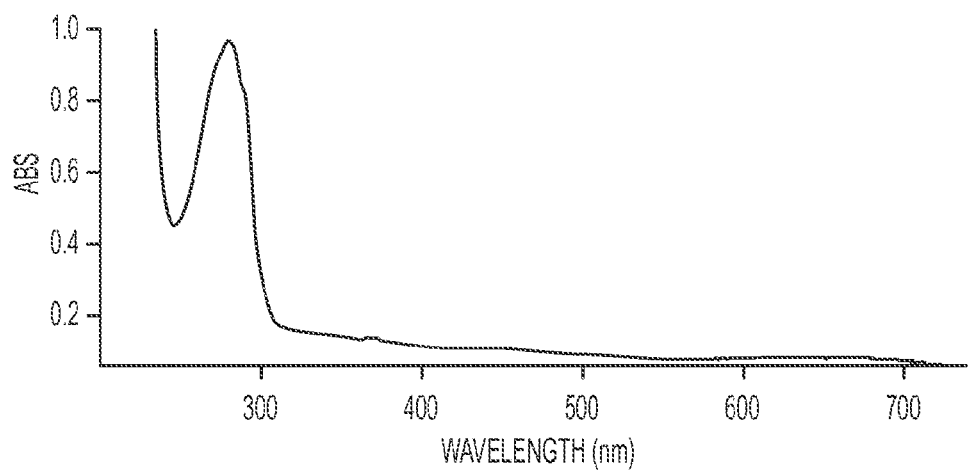
FIGS. 7A, 7B and 7C show a representative UV-VIS spectrum of a Cu(II)(AlaMetAspTrp) catalyst with oxygen.
Figure 7B:
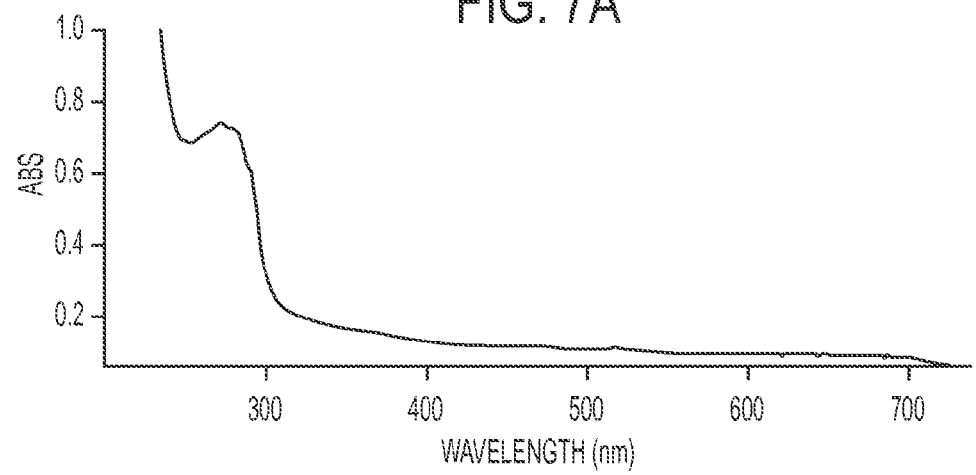
Figure 7C:
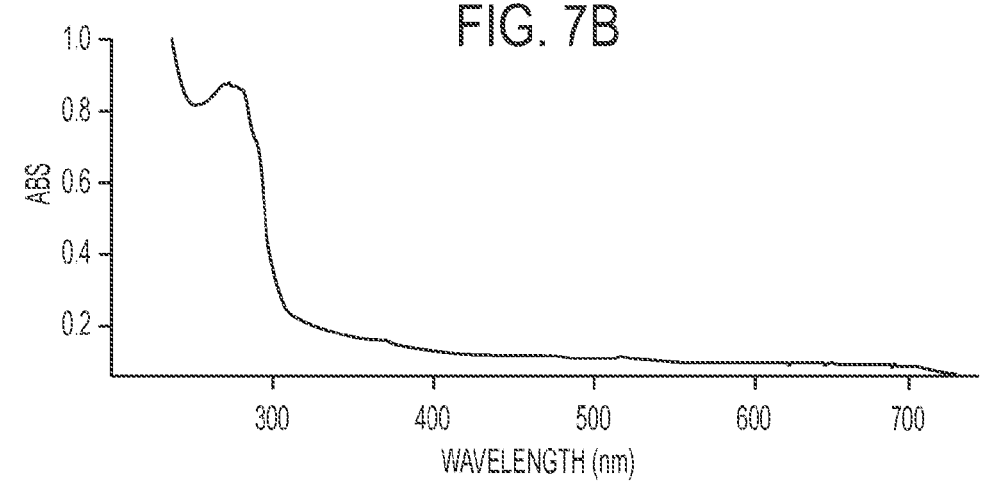

FIGS. 7A, 7B and 7C show UV-VIS spectra which confirms the generation of the Cu(II)(AlaMetAspTrp) catalyst in the presence of oxygen. The UV-VIS spectra showing the introduction of copper to the reaction shows a shift from 279.9 nm to 271.0 nm indicative of a copper complex formation.

A catalyst containing copper and peptide was prepared by conventional in situ complexation as described in Example 2 and 4. Results for the conventional in situ complexation to form the catalyst of this invention are shown in FIGS. 1-2 and 5-7. The catalyst was tested for its ability to catalytically oxidize methane to methanol. The results for using peptide copper catalysts for the oxidation of hydrocarbons are shown in FIGS. 3-4.

The terms and expressions that are used herein are meant for description not limitation, it being recognized that there may be minor changes or modifications that must take place and be within the scope of the present invention.

We claim:

1. A catalyst containing a copper metal and a peptide, wherein the peptide is a tetrapeptide or pentapeptide capable of catalytic oxidation of a hydrocarbon.

2. The catalyst in claim 1, wherein the peptide is a tetrapeptide.

3. The catalyst in claim 2, wherein the tetrapeptide is a straight chain tetrapeptide comprising four amino acids.

4. The catalyst in claim 3, wherein the straight chain tetrapeptide comprises four amino acids selected from the group consisting of Alanine, Aspartate, Glutamate, Glycine, Histidine, Methionine and Tryptophan.

5. The catalyst in claim 3, wherein the straight chain tetrapeptide comprises four amino acids selected from the group consisting of Alanine, Aspartate, Glutamate, Histidine, Methionine and Tryptophan.

6. The catalyst in claim 5, wherein the straight chain tetrapeptide comprises four amino acids selected from the group consisting of Alanine, Glutamate and Histidine.

7. The catalyst in claim 5, wherein the straight chain tetrapeptide comprises four amino acids selected from the group consisting of Alanine, Aspartate, Methionine and Tryptophan.

8. The catalyst in claim 3, wherein the straight chain tetrapeptide comprises four amino acids having at least Glutamate and Histidine.

9. The catalyst in claim 3, wherein the peptide is selected from any one of the following straight chain tetrapeptides having a peptide sequence comprising: AlaHisAlaGlu; AlaMetAspTrp; AlaHisGlyGlu; AlaHisHisHis; GlyHisHisHis; GluHisAspHis; HisMetAspTrp; and AspHisAspHis.

10. The catalyst in claim 3, wherein the peptide is selected from any one of the following straight chain tetrapeptides having a peptide sequence comprising: AlaHisAlaGlu; and AlaMetAspTrp.

11. A method for catalytic oxidation of a hydrocarbon using a catalyst containing a copper metal and a peptide, wherein the peptide is a tetrapeptide or pentapeptide capable of catalytic oxidation of a hydrocarbon.

12. The method in claim 11, wherein the peptide is a tetrapeptide.

13. The method in claim 12, wherein the tetrapeptide is a straight chain tetrapeptide comprising four amino acids.

14. The method in claim 13, wherein the straight chain tetrapeptide comprises four amino acids selected from the group consisting of Alanine, Aspartate, Glutamate, Glycine, Histidine, Methionine and Tryptophan.

15. The method in claim 13, wherein the straight chain tetrapeptide comprises four amino acids selected from the group consisting of Alanine, Aspartate, Glutamate, Histidine, Methionine and Tryptophan.

16. The method in claim 15, wherein the straight chain tetrapeptide comprises four amino acids selected from the group consisting of Alanine, Glutamate and Histidine.

17. The method in claim 15, wherein the straight chain tetrapeptide comprises four amino acids selected from the group consisting of Alanine, Aspartate, Methionine and Tryptophan.

18. The method in claim 13, wherein the straight chain tetrapeptide comprises four amino acids having at least Glutamate and Histidine.

19. The method in claim 11, wherein the peptide is selected from any one of the following tetrapeptides having a peptide sequence comprising: AlaHisAlaGlu; AlaMetAspTrp; AlaHisGlyGlu; AlaHisHisHis; GlyHisHisHis; GluHisAspHis; HisMetAspTrp; and AspHisAspHis.

20. The method in claim 11, wherein the peptide is selected from any one of the following tetrapeptides having a peptide sequence comprising: AlaHisAlaGlu; and AlaMetAspTrp.

21. The method in claim 11, wherein the hydrocarbon is methane or ethane.

22. The method in claim 11, wherein the hydrocarbon is methane.

23. The method in claim 11, wherein the catalytic oxidation is performed with water and oxygen gas at ambient temperature and pressure.

24. The method in claim 11, wherein the catalytic oxidation is performed with water and oxygen gas.

25. The method in claim 11, wherein the catalytic oxidation is performed at ambient temperature and pressure.

26. The method in claim 24, wherein the water is distilled or heavy water ($D_2O$).

27. The method in claim 21, wherein the methane is catalytically oxidized to methanol.

28. The method in claim 21, wherein the ethane is catalytically oxidized to ethanol.

* * * * *